(12) United States Patent
Bennett

(10) Patent No.: US 8,006,953 B2
(45) Date of Patent: Aug. 30, 2011

(54) LUER HUB CONNECTOR

(76) Inventor: LaVon Bennett, Mesa, AZ (US)

( * ) Notice: Subject to any disclaimer, the term of this patent is extended or adjusted under 35 U.S.C. 154(b) by 0 days.

(21) Appl. No.: 12/151,889

(22) Filed: May 9, 2008

(65) Prior Publication Data

US 2008/0287921 A1   Nov. 20, 2008

Related U.S. Application Data

(60) Provisional application No. 60/930,900, filed on May 17, 2007.

(51) Int. Cl.
*F16L 37/28* (2006.01)

(52) U.S. Cl. ............ 251/149.1; 251/149.6; 604/167.04; 604/537

(58) Field of Classification Search ............... 251/149.6, 251/149.1; 604/905, 533, 523, 26, 264, 167.02–167.04
See application file for complete search history.

(56) References Cited

U.S. PATENT DOCUMENTS

| | | | |
|---|---|---|---|
| 4,143,853 A | 3/1979 | Abramson | |
| 4,387,879 A | 6/1983 | Tauschinski | |
| 5,062,836 A * | 11/1991 | Wendell | 604/263 |
| 5,064,416 A | 11/1991 | Newgard et al. | |
| 5,300,034 A * | 4/1994 | Behnke et al. | 604/167.02 |
| 5,312,363 A | 5/1994 | Ryan et al. | |
| 5,456,675 A * | 10/1995 | Wolbring et al. | 604/256 |
| 5,464,400 A | 11/1995 | Collins | |
| 5,584,808 A * | 12/1996 | Healy | 604/905 |
| 5,989,233 A | 11/1999 | Yoon | |
| 6,113,068 A * | 9/2000 | Ryan | 251/149.6 |
| 6,482,188 B1 | 11/2002 | Rogers et al. | |
| 6,651,956 B2 | 11/2003 | Miller | |
| 6,669,681 B2 | 12/2003 | Jepson et al. | |
| 6,971,390 B1 | 12/2005 | Vasek et al. | |
| 7,140,592 B2 | 11/2006 | Phillips | |
| 2004/0143219 A1 * | 7/2004 | Lee et al. | 604/167.03 |
| 2007/0043334 A1 * | 2/2007 | Guala | 604/533 |
| 2008/0140055 A1 | 6/2008 | Shirley | |

OTHER PUBLICATIONS

International Search Report and Written Opinion dated Apr. 20, 2010 for PCT/US2010/23491.

* cited by examiner

*Primary Examiner* — John Fristoe, Jr.
*Assistant Examiner* — Andrew Rost
(74) *Attorney, Agent, or Firm* — Stoel Rives LLP

(57) ABSTRACT

A luer hub connector comprises a hub having a cylindrical bore extending there through. The hub is adapted to have a luer device connected at one end. A cap having a hollow nozzle extending therefrom is formed at the other end of the hub. A cylindrical spring-like member is positioned within the bore in the hub, and a septum membrane closes the end of the spring-like member. A sliding, hollow sleeve member is received in the bore of the hub member, with a hollow nozzle extending from the sleeve member into the bore of the spring-like member. When a luer device is threaded onto the end of the hub, it contacts and drives the sleeve member towards the septum. The end of the hollow nozzle is pushed through the septum, and the spring-like member is also compressed. When the luer device is removed, the spring-like member pushes the sleeve member back, and the hollow nozzle withdraws out of contact with the septum. The septum then closes and seals.

19 Claims, 2 Drawing Sheets

LUER HUB CONNECTOR

CROSS REFERENCE TO RELATED APPLICATION

This application claims the priority from U.S. Provisional Patent Application No. 60/930,900 filed on May 17, 2007.

BACKGROUND OF THE INVENTION

1. Field of the Invention

This invention relates to connector devices having a one-way septum valve. Connector devices employing such one-way septum valves provide a sterile closure for use with I.V. and syringe systems, and the one-way valve also prevents blood leakage from the patient back through the connector.

2. State of the Art

Prior art connectors have been proposed, but they tend to be complicated and generally ineffective. It would be desirable to provide a simple and inexpensive luer hub connector for use with an I.V. unit, syringe, and the like, with the connector having a reliable and trustworthy one-way septum valve having good sealing and sterility properties and which can be used a number of times while still maintaining these properties.

Representative of the prior art devices having a one-way septum valve is the connector device shown in U.S. Pat. No. 4,842,591. In that patent a connector and assembly for an I.V. unit, syringe is disclosed that includes a deformable slit septum in the form of a flat membrane made of a resilient polymeric material. A moveable, hollow plug is positioned a short distance from the septum. When the syringe tip is inserted into the connector and contact is made between the plug and the syringe tip, the plug is pushed inwardly and engages the slit of the septum and outwardly deforms the septum slightly. This permits liquid to flow through the septum to the patient. When the syringe tip is withdrawn from the connector, the septum is supposed to return to its generally flat condition and assume its initial closed state. This supposedly will cause the septum to reseal and prevent the backward flow of blood, etc., from the patient through the connector. Unfortunately it has been found that the resiliency of the septum is insufficient to guarantee the return of the septum to its initial closed state. The reliability of the connector and all other similar devices utilizing a septum in the form of a generally flat disc is not very good, and the devices have not found to be commercially acceptable.

BRIEF DESCRIPTION OF THE INVENTION

In accordance with the present invention, an improved luer hub connector having a one-way septum valve is disclosed. The improved luer hub connector comprises a novel one-way septum valve system that prevents the backward flow of blood and body fluids through the connector when an injection device such as a syringe, I.V. unit, and the like is removed from the luer hub connector. The novel one-way septum valve system of the invention has also been found to exhibit exceptional, unexpected reliability. The one-way septum valve system returns to its closed state without fail. The valve system includes a hub member having a cylindrical bore extending through the hub member from a proximal end thereof to a distal end thereof. A cylindrical, hollow extension extends outwardly from the proximal end of the hub member. The cylindrical extension has a bore that opens into the bore in the hub member, with the two bores being aligned coaxially. A flange or an external thread is formed at the distal end of the cylindrical extension so that the distal end of the cylindrical extension forms a male portion that can engage with a female counterpart of a luer locking type device.

A cap member is formed at the distal end of the hub member, with a hollow nozzle extending from the cap member in coaxial alignment with the bore in the hub member. A cylindrical spring-like member formed from a resilient polymer material is positioned within the bore in the hub member, with the spring-like member having a cylindrical bore that is in coaxial alignment with the bore in the hub member. A septum or membrane is formed integrally with the spring-like member, with the septum or membrane closing the end of the spring-like member at its end facing the cap member. A cylindrical, sliding sleeve member having a cylindrical bore is received in the bore of the cylindrical extension. The sleeve member has a hollow nozzle extending from its distal end into the bore of the spring-like member.

When a cooperating luer locking device is threaded onto the distal end of the cylindrical extension, the inner projecting tip of the luer locking device contacts the sleeve member and drives the sleeve member towards the septum at the end of the cylindrical spring-like member. The end of the hollow nozzle of the sleeve member is pushed through the septum so that fluid from an I.V. unit, syringe, etc., can be fed through the septum opening and into a patient. The sleeve member also compresses the cylindrical portion of the spring-like member as it moves towards the septum. When the luer locking device is retracted, the spring action of the spring-like member pushes the sleeve member back towards the distal end of the cylindrical extension, with the hollow nozzle of the sleeve member being withdrawn back through the septum and out of contact with the septum. The septum then closes and seals. The spring action of the spring-like member has been found to push the sleeve member back without fail, and to also result in the closing and sealing of the septum without fail.

DESCRIPTION OF THE PREFERRED EMBODIMENTS

Figure 1:
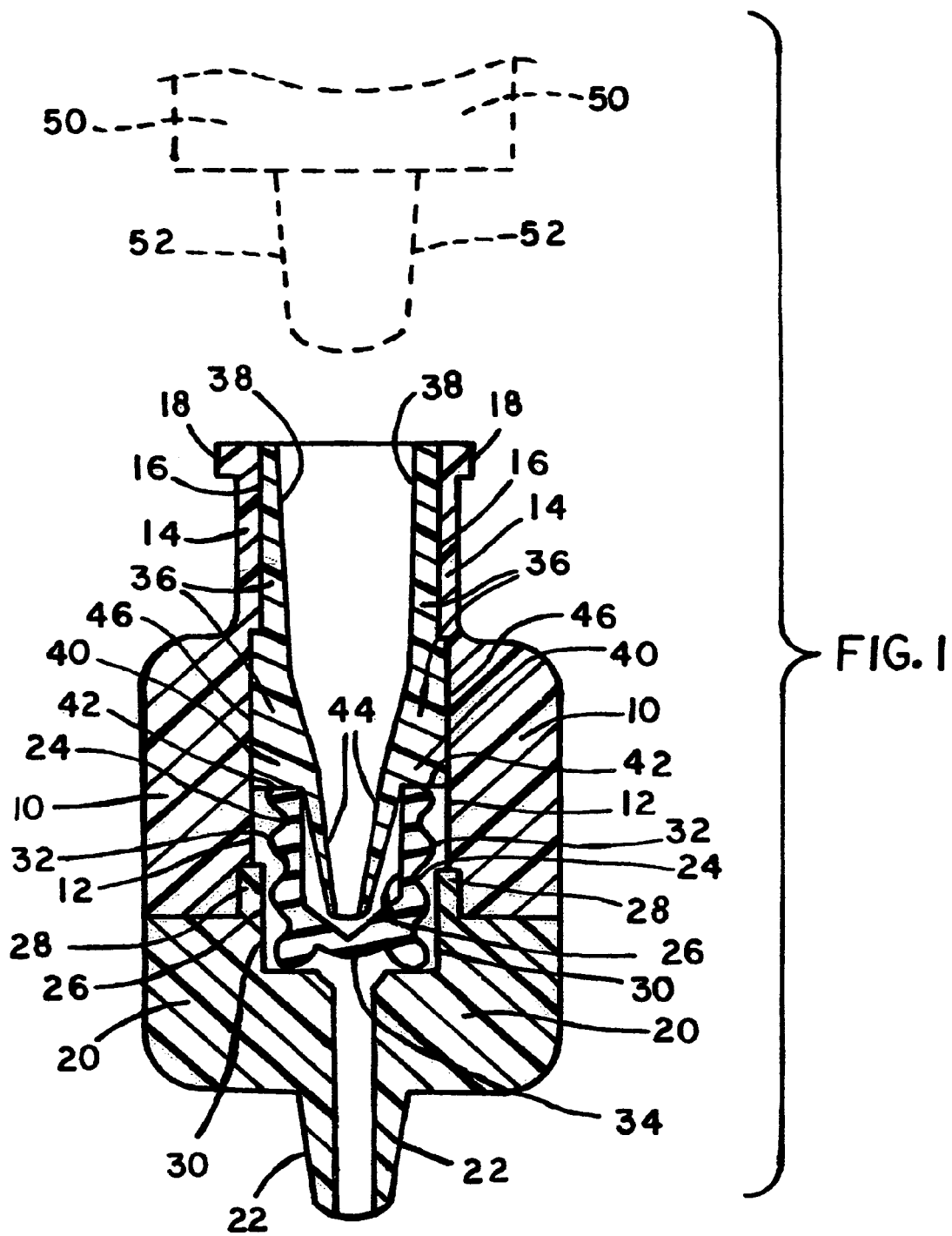
FIG. 1 is a cross-sectional view taken through a central axis of one embodiment of a luer hub connector having a one-way septum valve in accordance with the present invention.

As shown in the drawings, the luer hub connector includes a hub member 10 having a cylindrical bore 12 extending through the hub member 10 from a proximal end thereof to a distal end thereof. The hub member 10 is preferably molded from a polymeric material. A cylindrical, hollow extension 14 is preferably molded integrally with the hub member 10 and extends outwardly from the proximal end of the hub member 10. The cylindrical extension 14 has a cylindrical bore 16 that opens into the bore 12 in the hub member, with the two bores 12 and 16 being aligned coaxially. A flange 18 is shown in the drawings formed at the distal end of the cylindrical extension. The flange 18 can be replaced with a set of threads (not shown in the drawings, but conventionally known in the art). The flange 18 performs the same as a set of threads so that the distal end of the cylindrical extension 14 forms a male portion that can engage with a female counterpart of a luer locking type device.

A cap member 20 is positioned at the distal end of the hub member 10. The cap member 20 is preferably molded from the same polymer material as the hub member 10. The cap member 20 could if desired be molded integrally with the hub member 10, as will be hereinafter shown and described with respect to the embodiment shown in FIG. 2, but in the embodiment as illustrated in FIG. 1, the cap member 20 is molded as a separate piece. To attach the cap member 20 to the hub member 10 in the embodiment shown in FIG. 1, a thin-walled, cylindrical extension 28 can extend from the face thereof that abuts the distal end of the hub member 10. The thin-walled cylindrical extension 28 is received snugly within the bore 12 in the distal end of the hub member 10, and can be glued or solvent welded to the sidewall of bore 12. A relatively shallow well 30 can extend inwardly into the cap member 20 from the cylindrical extension 28, as illustrated in FIG. 1, with the well 30 being in coaxial alignment with the cylindrical extension 28 and having a diameter that is the same as the inner diameter of the cylindrical extension 28. It should be appreciated, however, that the well 30 is not per-se necessary. The end of the hub member 10 could extend downward further than shown in FIG. 1, so that the abutting faces of the hub member 10 and cap member 20 would coincide with the position of the bottom of the shallow well 30 of the embodiment shown in FIG. 1.

The cap member 20 further has a hollow nozzle 22 extending therefrom. The hollow nozzle 22 is preferably, but not necessarily, in coaxial alignment with the bore 12 in the hub member 10. The inner end of the hollow nozzle 22 is open to the bore 12 so that fluid can flow from the bore 12 into the hollow nozzle 22. The lower end of the nozzle 22 is open and adapted to be attached in fluid flow relationship with a catheter or other flow channel as is well known in the art.

A one-way septum valve is provided, with the septum valve comprising in part a cylindrical spring-like member 24 that is formed from a resilient, elastomeric polymer material, preferably from silicone rubber. The spring-like member 24 is positioned within the bore 12 in the hub member 10, with the spring-like member 24 having a cylindrical opening 26 that extends longitudinally through the spring-like member 24, with the cylindrical opening 26 being in coaxial alignment with the bore 12 in the hub member 10. The spring-like member 24 is positioned longitudinally in the bore 12 of the cap member 20 and the shallow well 30 (if such a well is provided) of the cap member 20. The spring-like member 24 preferably is in the shape of a longitudinal cylinder with a plurality of circumferential rings or annuluses 32 that are spaced longitudinally along the outer surface of the longitudinal cylinder. The longitudinal cylinder of the spring-like member 24 is preferably between about 6 to 10 mm in length. There are preferably about 3 or 4 rings or annuluses 32, with the rings or annuluses 32 being molded integrally with the longitudinal cylinder of the spring-like member 24, and, of course, the rings or annuluses 32 and the longitudinal cylinder of the spring-like member 24 are formed of the same resilient, elastomeric polymer, preferably silicone rubber. Each of the rings or annuluses 32 have a thickness of from about 0.75 to 1.25 mm, preferably about 1 mm, and each of the rings or annuluses 32 extend outwardly from the external surface of the longitudinal cylinder of the spring-like member 24 by about the same distance as their thickness.

The one-way septum valve is completed by providing a septum or membrane 34 that is formed integrally with the spring-like member 24, with the septum or membrane 34 closing the cylindrical opening 26 at an end of the spring-like member 24 that faces the cap member 20. The septum or membrane 34 is molded integrally with the other parts of the spring-like member 24 and, of course, of the same resilient, elastomeric polymer, preferably silicone rubber.

A cylindrical, sliding sleeve member 36 is received for longitudinal sliding movement within the bores 16 and 12 of the cylindrical extension 14 and hub member 10, respectively. The sleeve member 36 has an inner bore 38 that tapers from an open, upper end of the sleeve member 36 towards the lower end of the sleeve member 36. The taper on the inner bore 38 matches the shape of the projecting nozzle tip 52 of a luer lock device 50 (the luer lock device 50 is shown in the drawings in phantom inasmuch as it does not form a part of the luer lock connector of the present invention, and such a conventional luer lock device 50 is so well known and understood in the art that no further description need be included herein). When the luer lock device is screwed onto the cylindrical extension 14 of the hub member 10, the projecting nozzle tip of the luer lock device engages the inner bore 38 of the sliding sleeve member 36 and pushes the sliding sleeve member 36 inwardly into the hub member 10 towards the cap member 20.

The sliding sleeve member 36 has a thicker, lower end portion 40 at the leading end of the sleeve member 36, with the lower end portion 40 forming a circumferential, substantially flat bottom surface 42. A hollow nozzle 44 extends from the bottom surface 42 of the sliding sleeve member 36 into the bore 26 of the spring-like member 24. The hollow nozzle 44 is open at its upper end for fluid flow from the inner bore 38 of the sliding sleeve member 36. When a conventional luer locking device 50 is threaded onto the distal end of the cylindrical extension 14 of the hub member 10, the projecting nozzle tip 52 of the luer locking device 50 contacts the inner bore 38 of the sliding sleeve member 36 and drives the sleeve member 36 towards the septum membrane 34 at the end of the cylindrical spring-like member 24. The pointed end of the hollow nozzle 44 of the sleeve member 36 is pushed through the septum membrane 34 so that fluid from an I.V. unit, syringe, etc., can be fed through the hollow nozzle 44 past the septum membrane 34 and into a patient.

The flat bottom surface 42 of the inner end 40 of the sleeve member 36 contacts the upper end of the spring-like member 24 and pushes it toward the cap member 20. The cylindrical portion of the spring-like member 24 is compressed by the movement of the sleeve member 36 as it moves towards the septum membrane 34. The rings or annuluses 32 on the cylindrical portion of the spring-like member are compressed against each other and supply additional spring-like force or bias to the spring-like member 34. When the luer locking device is retracted and removed from the cylindrical extension 14 of the hub member 10, the spring action of the spring-like member 24 pushes the sleeve member 36 back towards the distal end of the cylindrical extension 14, with the hollow nozzle 44 of the sleeve member 36 being withdrawn back through the septum membrane 34 and out of contact with the septum membrane 34. The septum membrane 34 then closes and seals thus preventing back flow of blood or other body fluid into the bore 12 of the hub member 10. The spring action of the spring-like member 24 has been found to push the sleeve member 36 back without fail, and to also result in the closing and sealing of the septum membrane 34 without fail. The septum membrane 34 is preferably formed with a convex surface facing outwardly from the spring-like member 24 toward the cap member 20. The convex surface of the septum membrane 34 aids in the closing and sealing of the septum membrane 34. The closing of the septum membrane 34 is achieved without fail, and the luer connector member of the present invention can be used innumerable times with the septum membrane 34 never failing to close and seal when the sliding sleeve member 36 is pushed back so that the hollow nozzle 44 is retracted out of contact with the septum membrane 34.

As explained above, when the cooperating luer locking device 50 is threaded onto the distal end of the cylindrical extension 14 of the hub member 10, the sliding sleeve member 36 is driven toward the septum membrane 34. When the sleeve member 36 has been moved to its optimum desired position, a lower edge of the enlarged section 46 of the sleeve member 36 will abut and in essence seat against the upper edge of the cylindrical extension 28 of the cap member 20. The abutting of the sleeve member 36 with the upper edge of the cylindrical extension 28 forms a stop that can be sensed by the doctor or clinical personnel who is attaching the luer locking device to the hub connector 10 of the present invention. Sensing of the stop is advantageous inasmuch as it gives the doctor or clinical personnel assurance that the luer locking device has been properly attached to the hub connector 10.

The sliding sleeve member 36 is retained in the hub member 10 so that the sleeve member 36 cannot escape from the open end of the extension member 14. As shown in the embodiment illustrated in FIG. 1, one way of retaining the sleeve member 36 in the hub member 10 is to provide an annular ring 46 around the outer surface of the sliding sleeve member 36. The annular ring 46 is positioned so that it contacts the lower end of the extension member 14 when the sliding sleeve member 36 is at its desired position as it is pushed upwardly by the spring-like member 24. The second way of retaining the sleeve member 36 in the hub member 10 will be described below with reference to a modified embodiment of the luer hub connector of the present invention.

Figure 2:
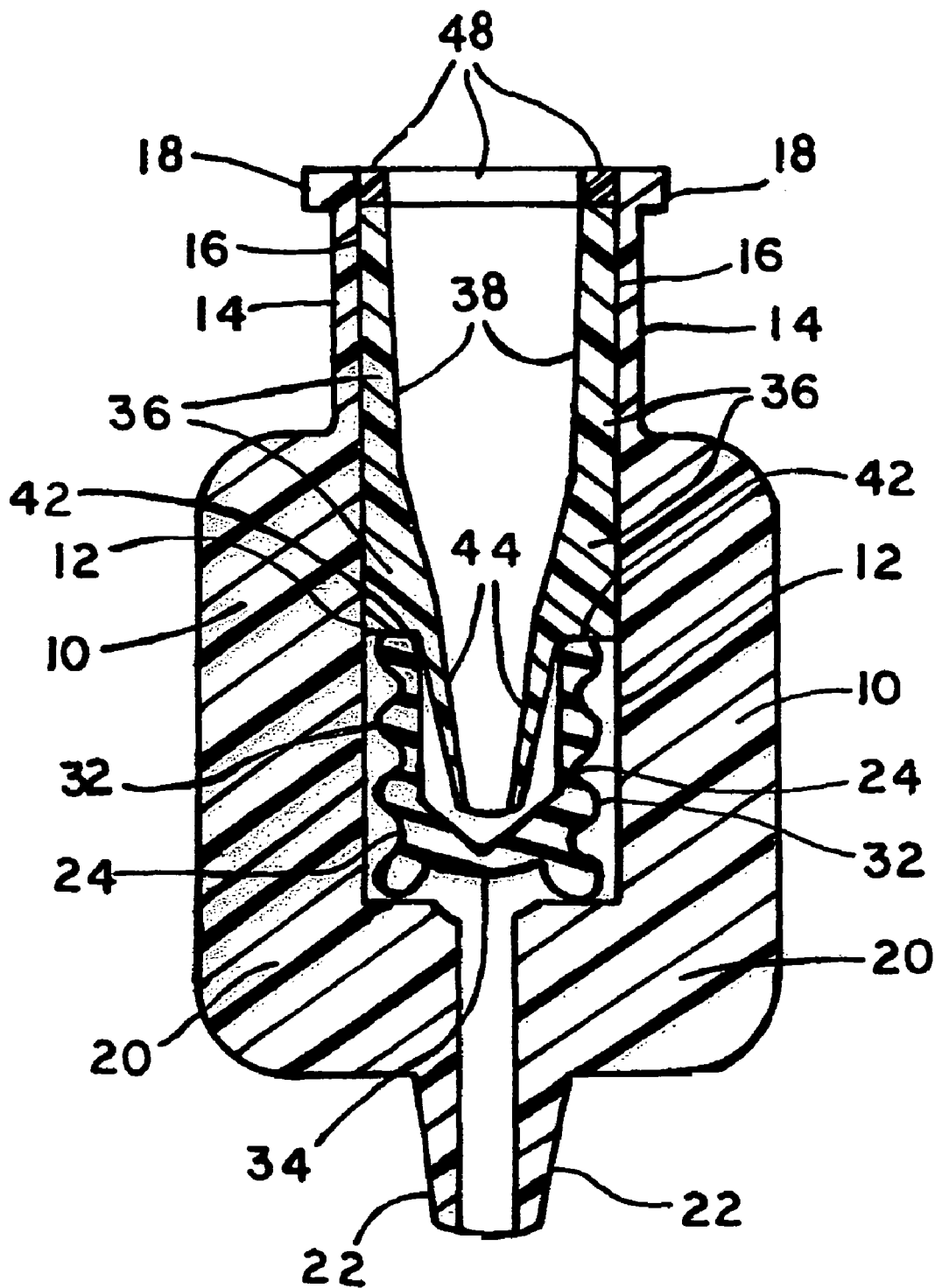
FIG. 2 is a cross-sectional view similar to that of FIG. 1 but showing a slightly modified embodiment of the hub connector of the present invention.

The embodiment of the invention shown in FIG. 2 is very similar to the embodiment shown in FIG. 1. All reference numbers used for the description of the embodiment of FIG. 1 are shown on the same or similar members in the embodiment shown in FIG. 2. Only the changes and modification of those members of the embodiment of FIG. 2 will be discussed rather than a redundant recitation of the entire invention. In the embodiment of the invention as shown in FIG. 2, the cap member 20 is molded integrally with the hub member 10. The size, i.e., diameter, of the bore 16 in the extension member 14 that extends from the hub member 10 is the same as that of the bore 12 of the hub member 10. The bores 12 and 16 make a continuous sized, cylindrical channel that extends from the open end of the extension member 14 downwardly to the cap member 20. The spring-like member 24 is fit in that channel and rests at the bottom of the channel on the cap member 20. The sliding sleeve member 36 is then introduced down the channel to make engagement with the upper end of the spring-like member 24. The sliding sleeve member 36 is held in the connector hub by a narrow flange 48 that extends inwardly from the open end of the extension member 14. The narrow flange 48 is positioned after the spring-like member 24 and the sliding sleeve member 36 have been introduced into the cylindrical channel in the connector hub. It should be pointed out that the flange 48 as shown in FIG. 2 could also be used in the embodiment of the invention shown in FIG. 1. A flange similar to the flange 48 of FIG. 2 would have been formed integrally with the open end of the extension member 14 of FIG. 1. There would be no reason to incorporate the ring 46 around the sleeve member 36 as shown in FIG. 1. That ring 46 would simply be eliminated, and a flange similar to the flange 48 of the embodiment of FIG. 2 would perform the function of the ring 46.

Although preferred embodiments of the luer hub connector of the present invention have been illustrated and described, it is to be understood that the present disclosure is made by way of example and that various other embodiments are possible without departing from the subject matter coming within the scope of the invention.

The invention claimed is:

1. A luer hub connector for use with an injection device, the luer hub connector configured to automatically close when the injection device is decoupled from the luer hub connector to control the backward flow of blood and body fluids through the connector, the luer hub connector comprising:
   a body member having a proximal end and distal end;
   a cylindrical bore extending along the length of the body member from a proximal end to a distal end thereof;
   a one-way septum valve positioned within the cylindrical bore so as to selectively control the flow of fluids through the cylindrical bore, the one-way septum valve comprising a longitudinal cylinder and having a proximal end, a distal end, an outside diameter, an inside diameter, and a plurality of annuluses integrally formed with the longitudinal cylinder, the plurality of annuluses arranged in a repeating, wave-like pattern where each annulus of the plurality of annuluses extends outwardly from the outside diameter of the longitudinal cylinder and the inside diameter of the longitudinal cylinder is substantially constant along a longitudinal length of the cylinder which spans between at least two annuluses, and wherein the annuluses are configured to compress against each other when a compressive force is applied to the septum valve, the compression of the annuluses thereby providing a resilient biasing force in the opposite direction of the compressive force, and wherein one or more annuluses are positioned in the proximal end of the one-way septum valve, wherein a first annulus is positioned at the distal end of the one-way septum valve, the first annulus configured to contact a surface at the distal end of the cylindrical bore, thereby biasing the septum valve in the closed position, and wherein a septum is positioned between the proximal end and the distal end such that the septum can be opened by interaction with a secondary member which exerts a compressive or dialatory force on the one-way septum valve and the septum will close in response to removal of the compressive or dialatory force on the one-way septum valve.

2. The luer hub connector of claim 1, wherein the body member comprises a hub member.

3. The luer hub connector of claim 2, wherein the body member further comprises a cap member.

4. The luer hub connector of claim 3, wherein the cap member is integrally coupled to the hub member to form the cylindrical bore.

5. The luer hub connector of claim 4, wherein the cap member includes a shallow well corresponding with the cylindrical bore and a hollow nozzle, the shallow well adapted to receive at least a portion of the one-way septum valve such that the one-way septum valve is positioned between the hollow nozzle and the secondary member positioned within at least a portion of the cylindrical bore associated with the hub member.

6. A luer hub connector for use with an injection-device, the luer hub connector configured to automatically close when the injection device is decoupled from the luer hub connector to control the backward flow of blood and body fluids through the connector, the luer hub connector comprising;
   a body member having a proximal end and distal end;
   a cylindrical bore extending along the length of the body member from a proximal end to a distal end thereof;
   a one-way septum valve positioned within the cylindrical bore so as to selectively control the flow of fluids through the cylindrical bore, the one-way septum valve comprising a longitudinal cylinder and having a proximal end, a distal end, an outside diameter, an inside diameter, and a plurality of annuluses integrally formed with the longitudinal cylinder, the plurality of annuluses arranged in a repeating, wave-like pattern where each annulus of the plurality of annuluses extends outwardly from the outside diameter of the longitudinal cylinder and the inside diameter of the longitudinal cylinder is substantially constant along a longitudinal length of the cylinder which spans between at least two annuluses, and wherein the annuluses are configured to compress against each other when a compressive force is applied to the septum valve, the compression of the annuluses thereby providing a resilient biasing force in the opposite direction of the compressive force, and wherein one or more annuluses are positioned in the proximal end of the one-way septum valve, wherein a first annulus is positioned at the distal end of the one-way septum valve, the first annulus configured to contact a surface at the distal end of the cylindrical bore, thereby biasing the septum valve in the closed position, and wherein a septum is positioned between the proximal end and the distal end such that the septum can be opened by interaction with a secondary member which exerts a compressive or dialatory force on the one-way septum valve and the septum will close in response to removal of the compressive or dialatory force on the one-way septum valve; and a cylindrical sliding sleeve member slidably positioned within the cylindrical bore adjacent a luer coupling on the proximal end of the body member.

7. The luer hub connector of claim 6, wherein the cylindrical sliding sleeve member includes a tapered inner bore.

8. The luer hub connector of claim 7, wherein when a luer device is threaded onto the luer hub connector, a projecting nozzle tip of the luer device engages the tapered inner bore of the sliding sleeve member urging the sliding sleeve member in a forward direction.

9. The luer hub connector of claim 8, wherein the advancement of the sliding sleeve member causes the sliding sleeve member to engage the one-way septum valve causing opening of the septum and allowing the flow of fluids through the one-way septum valve.

10. The luer hub connector of claim 9, wherein when the luer device is decoupled from the luer hub connector, the sliding sleeve member is urged out of engagement with the one-way septum valve, the septum closes and seals, preventing or minimizing the flow of fluids through the cylindrical bore.

11. The luer hub connector of claim 6, wherein the sliding sleeve member includes a circumferential bottom surface.

12. The luer hub connector of claim 11, wherein the circumferential bottom surface is adapted to contact the upper end of the one way septum valve and compress the one way septum valve.

13. The luer hub connector of claim 12, wherein when the luer locking device is removed from the luer hub connector, the spring action of the one-way septum valve pushes the sliding sleeve member to a position in which it is no longer compressing the one-way septum valve.

14. A luer hub connector for use with an injection device, the luer hub connector configured to automatically close when the injection device is decoupled from the luer hub connector to control the backward flow of blood and body fluids through the connector, the luer hub connector comprising;

a body member having a proximal end and a distal end;

a cylindrical bore extending along the length of the body member from a proximal end to a distal end thereof, the body member comprising a hub member forming the proximal end of the body member and a cap member comprising the distal end of the body member;

a one-way septum valve positioned within the cylindrical bore so as to selectively control the flow of fluids through the cylindrical bore, the one-way septum valve comprising a longitudinal cylinder and having a proximal end, a distal end, an outside diameter, an inside diameter, and a plurality of annuluses integrally formed with the longitudinal cylinder, the plurality of annuluses arranged in a repeating, wave-like pattern where each annulus of the plurality of annuluses extends outwardly from the outside diameter of the longitudinal cylinder and the inside diameter of the longitudinal cylinder is substantially constant along a longitudinal length of the cylinder which spans between at least two annuluses, and wherein the annuluses are configured to compress against each other when a compressive force is applied to the septum valve, the compression of the annuluses thereby providing a resilient biasing force in the opposite direction of the compressive force, and wherein one or more annuluses are positioned in the proximal end of the one-way septum valve, wherein a first annulus is positioned at the distal end of the one-way septum valve, the first annulus configured to contact a surface of the cap member at the distal end of the cylindrical bore, thereby biasing the septum valve in the closed position, and wherein a septum is positioned between the proximal end and the distal end such that the septum can be opened by interaction with a secondary member which exerts a compressive or dialatory force on the one-way septum valve and the septum will close in response to removal of the compressive or dialatory force on the one-way septum valve.

15. The luer hub connector of claim 14, wherein the hub member includes a cylindrical extension having a plurality of threads for coupling the luer hub connector to a secondary luer locking device.

16. The luer hub connector of claim 14, wherein the one-way septum valve comprises a resilient spring-like member.

17. The luer hub connector of claim 16, wherein the annuluses contribute to the resilient force provided by compression of the one-way septum valve.

18. The luer hub connector of claim 17, wherein the seal of the one-way septum valve can be temporarily be broken by either, one of or a combination of a needle or other elongate instrument and a secondary luer locking device.

19. The luer hub connector of claim 3, wherein the surface configured to be contacted by the annulus is a surface of the cap member.

* * * * *